United States Patent
Narimatsu et al.

(10) Patent No.: US 6,884,221 B2
(45) Date of Patent: Apr. 26, 2005

(54) CIRCULATORY-ORGAN EVALUATING APPARATUS

(75) Inventors: Kiyoyuki Narimatsu, Komaki (JP); Toshihiko Ogura, Komaki (JP); Akira Tampo, Komaki (JP)

(73) Assignee: Colin Medical Technology Co Corporation, Komaki (JP)

(*) Notice: Subject to any disclaimer, the term of this patent is extended or adjusted under 35 U.S.C. 154(b) by 123 days.

(21) Appl. No.: 10/370,617

(22) Filed: Feb. 24, 2003

(65) Prior Publication Data

US 2003/0236464 A1 Dec. 25, 2003

(30) Foreign Application Priority Data

Jun. 20, 2002 (JP) ......................................... 2002-180370

(51) Int. Cl.⁷ ............................... A61B 5/02; A61B 5/00
(52) U.S. Cl. ........................ 600/485; 600/483; 600/481; 600/300
(58) Field of Search ................................. 600/481, 483, 600/485, 486, 490, 492–496, 500–503, 508–526

(56) References Cited

U.S. PATENT DOCUMENTS

| | | |
|---|---|---|
| 5,265,011 A | 11/1993 | O'Rourke |
| 5,743,856 A | 4/1998 | Oka et al. |
| 6,196,974 B1 | 3/2001 | Miwa |
| 6,322,516 B1 | 11/2001 | Masuda et al. |
| 6,440,079 B1 * | 8/2002 | Ogura et al. ................. 600/492 |
| 6,612,993 B1 * | 9/2003 | Narimatsu ................... 600/500 |
| 6,659,958 B1 * | 12/2003 | Narimatsu et al. .......... 600/485 |
| 6,666,827 B1 * | 12/2003 | Narimatsu ................... 600/490 |
| 6,702,754 B1 * | 3/2004 | Ogura et al. ................. 600/500 |
| 6,712,768 B1 * | 3/2004 | Ogura et al. ................. 600/494 |
| 6,719,704 B1 * | 4/2004 | Narimatsu et al. .......... 600/500 |
| 6,746,405 B1 * | 6/2004 | Narimatsu ................... 600/494 |

FOREIGN PATENT DOCUMENTS

| | | |
|---|---|---|
| EP | 1 050 267 A1 | 11/2000 |
| JP | A 9-140679 | 6/1997 |
| JP | 11-045286 | 2/1999 |
| JP | 2001-069659 | 3/2001 |

OTHER PUBLICATIONS

Masuda, Y. "Basis of Pulse Wave, Waveform of Pressure Wave (Pulse Wave)," *Pulse Wave Velocity*, May 1, 2002, pp. 18–25, in Japanese and English translation pp 1–7.

* cited by examiner

*Primary Examiner*—Robert L. Nasser
*Assistant Examiner*—Navin Natnithithadha
(74) *Attorney, Agent, or Firm*—Oliff & Berridge

(57) ABSTRACT

A circulatory-organ evaluating apparatus for evaluating a circulatory organ of a living subject, including a display device, and a control device which controls the display device to simultaneously and graphically display a blood pressure, an augmentation index, and pulse-wave-velocity-related information of the subject.

6 Claims, 10 Drawing Sheets

CIRCULATORY-ORGAN EVALUATING APPARATUS

BACKGROUND OF THE INVENTION

1. Field of the Invention

The present invention relates to a circulatory-organ evaluating apparatus which evaluates a circulatory organ of a living subject.

2. Related Art Statement

The dynamic function of circulatory organ of a living person is primarily defined by the pumping function of the person's heart, and also is influenced by the degree of contraction or dilation of walls of blood vessels (e.g., the degree of hardness of arteries) or the diameter of blood vessels.

Therefore, the dynamic function of circulatory organ is evaluated by measuring, e.g., the person's blood pressure. If the person is diagnosed with hypertension, the person will undergo a medical treatment such as administration of antihypertensive drug. In addition, since the blood pressure is influenced by the degree of hardness of arteries, there will be some cases where pulse-wave-velocity-related information that is related to a velocity at which a pulse wave propagates between the person's two portions is obtained so as to evaluate the degree of hardness of arteries as well. Those evaluations may be made by, e.g., an apparatus disclosed by Japanese Patent Document No. 9-140679 or its corresponding U.S. Pat. No. 5,743,856.

Meanwhile, there are some indexes used for evaluating the circulatory organ of living person. Those indexes include, in addition to blood pressure and pulse-wave-velocity-related information, augmentation index, AI. The augmentation index indicates a proportion of a reflected-wave component of a pulse wave to an incident-wave component of the same. In order to accurately evaluate the circulatory organ, it is preferred to simultaneously measure augmentation index in addition to blood pressure and pulse-wave-velocity-related information, because the increased number of physical parameters obtained from the person can be used to evaluate the circulatory organ.

However, in the case where the circulatory organ is evaluated by measuring the three indexes, i.e., blood pressure, pulse-wave-velocity-related information, and augmentation index, if respective measured values of the three indexes are just displayed, it is difficult to speculate how pulse-wave-velocity-related information or augmentation index influences blood pressure, or conversely if blood pressure influences pulse-wave-velocity-related information or augmentation index. Thus, there are some cases where it is difficult to evaluate the circulatory organ if the three measured values are just displayed. In particular, in the case where a patient is informed of a therapy to be taken or of therapeutic effects, it is difficult for the patient to evaluate the circulatory organ based on only the measured values.

SUMMARY OF THE INVENTION

It is therefore an object of the present invention to provide a circulatory-organ evaluating apparatus which permits easy evaluation of the circulatory organ of a living subject.

The above object has been achieved by the present invention. According to the present invention, there is provided a circulatory-organ evaluating apparatus for evaluating a circulatory organ of a living subject, comprising a display device; and a control device which controls the display device to simultaneously and graphically display a blood pressure, an augmentation index, and pulse-wave-velocity-related information of the subject.

According to this invention, a person can graphically recognize, on the display device, the blood pressure, augmentation index, and pulse-wave-velocity-related information of the subject. Thus, the person is permitted to easily evaluate the circulatory organ of the subject.

According to a preferred feature of the present invention, the display device displays a multi-dimensional graph representing at least the blood pressure, the augmentation index, and the pulse-wave-velocity-related information of the subject. According to this feature, since the person can graphically recognize, from the single multi-dimensional graph, the three parameters, i.e., the blood pressure, the augmentation index, and the pulse-wave-velocity-related information, the person can easily evaluate the circulatory organ based on those increased number of parameters. However, the display device may display respective graphs of the blood pressure, the augmentation index, and the pulse-wave-velocity-related information, independent of each other.

According to another feature of the present invention, the multi-dimensional graph includes a standard figure representing a standard blood pressure, a standard augmentation index, and standard pulse-wave-velocity-related information. According to this feature, the person can more easily evaluate the circulatory organ by graphically comparing the measured values of the blood pressure, the augmentation index, and the pulse-wave-velocity-related information, with the standard figure.

According to another feature of the present invention, the multi-dimensional graph represents respective time-wise changes of the blood pressure, the augmentation index, and the pulse-wave-velocity-related information of the subject. According to this feature, since the person can graphically recognize the respective time-wise changes of the blood pressure, the augmentation index, and the pulse-wave-velocity-related information, the person can easily evaluate a time-wise change of the circulatory organ. Therefore, the person can easily evaluate the effect of medication or the improvement of subject's habits.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which:

FIG. 1 is a diagrammatic view showing a circuitry of a circulatory-organ evaluating apparatus to which the present invention is applied;

FIG. 2 is a view showing a state in which a pressure-pulse-wave detecting probe of the apparatus of FIG. 1 is worn on a cervical portion of a living subject;

FIG. 3 is an enlarged view of the pressure-pulse-wave detecting probe of FIG. 2, a portion of the probe being cut away;

FIG. 4 is a view for explaining a state in which an array of pressure sensing elements is provided in a press surface of a pressure-pulse-wave sensor shown in FIG. 3;

FIG. 5 is a view showing an example of a carotid pulse wave, wc, represented by a pressure-pulse-wave signal, SM2, supplied from one of the pressure sensing elements of the pressure-pulse-wave sensor of FIG. 3;

DETAILED DESCRIPTION OF PREFERRED EMBODIMENTS

Figure 1:
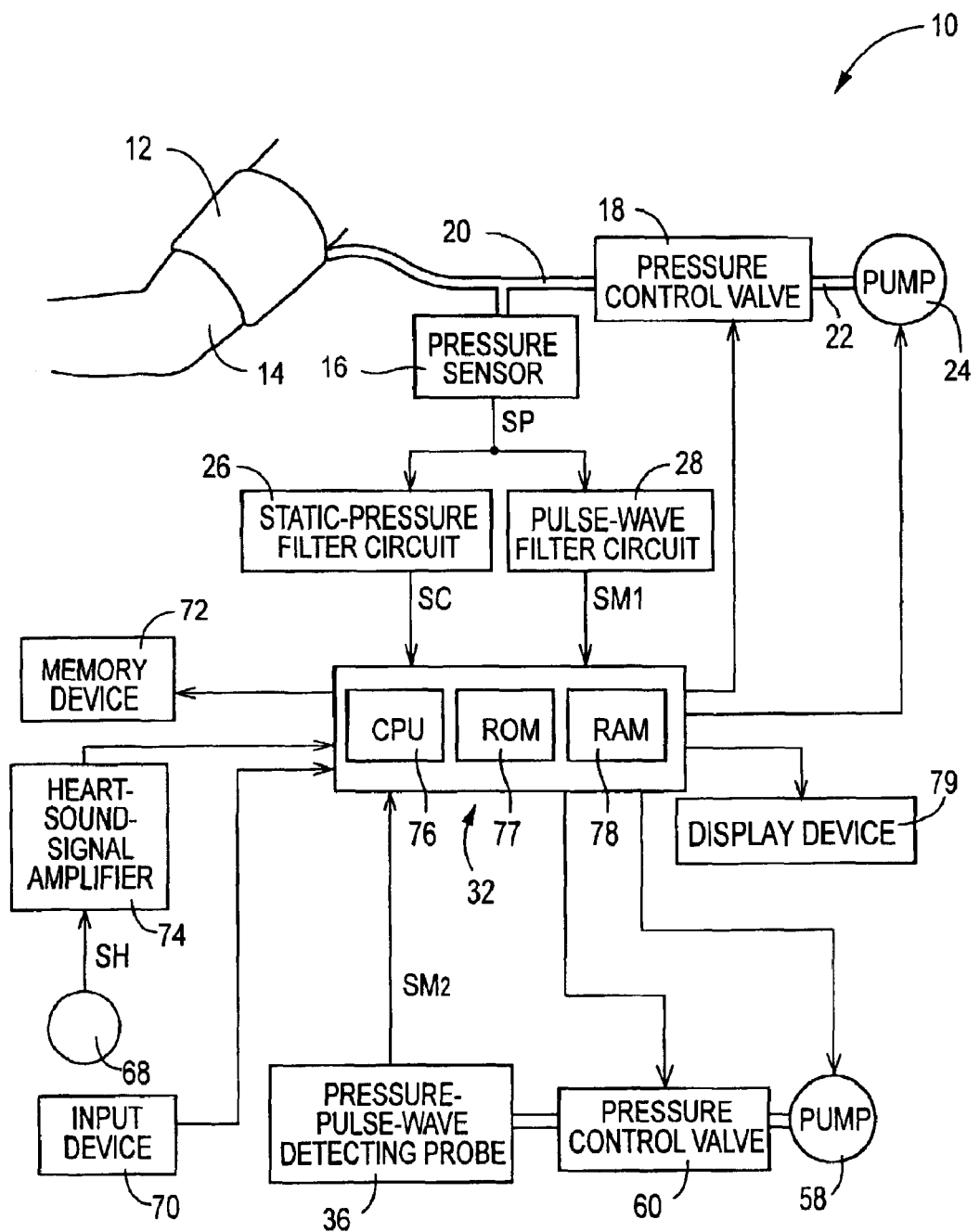

Hereinafter, there will be described an embodiment of the present invention in detail by reference to the drawings. FIG. 1 is a diagrammatic view showing a circuitry of a circulatory-organ evaluating apparatus 10 to which the present invention is applied.

In FIG. 1, reference numeral 12 designates an inflatable cuff which includes a belt-like cloth bag and a rubber bag accommodated in the cloth bag and which is adapted to be wound around a brachial portion 14 of a patient as a living subject. The cuff 12 is connected via a piping 20 to a pressure sensor 16 and a pressure control valve 18. The pressure control valve 18 is connected via a piping 22 to an air pump 24. The pressure control valve 18 adjusts a pressure of a pressurized air supplied from the air pump 24, and supplies the pressure-adjusted air to the cuff 12, or discharges the pressurized air from the cuff 12, so as to control an air pressure in the cuff 12.

The pressure sensor 16 detects the air pressure in the cuff 12, and supplies a pressure signal, SP, representing the detected air pressure, to a static-pressure filter circuit 26 and a pulse-wave filter circuit 28. The static-pressure filter circuit 26 includes a low-pass filter which extracts, from the pressure signal SP, a cuff-pressure signal, SC, representing a static component of the detected air pressure, i.e., a pressing pressure of the cuff 12 (hereinafter, referred to as the cuff pressure, PC). The filter circuit 26 supplies the cuff-pressure signal SC to an electronic control device 32 via an A/D (analog-to-digital) converter, not shown. The pulse-wave filter circuit 28 includes a band-pass filter which extracts, from the pressure signal SP, a cuff-pulse-wave signal, SM1, representing a cuff pulse wave as an oscillatory component of the detected air pressure. The filter circuit 28 supplies the cuff-pulse-wave signal SM1 to the control device 32 via an A/D converter, not shown. The cuff pulse wave represented by the cuff-pulse-wave signal SM1 is a brachial pulse wave, wb, produced from a brachial artery, not shown, of the patient that is pressed by the cuff 12.

Figure 2:
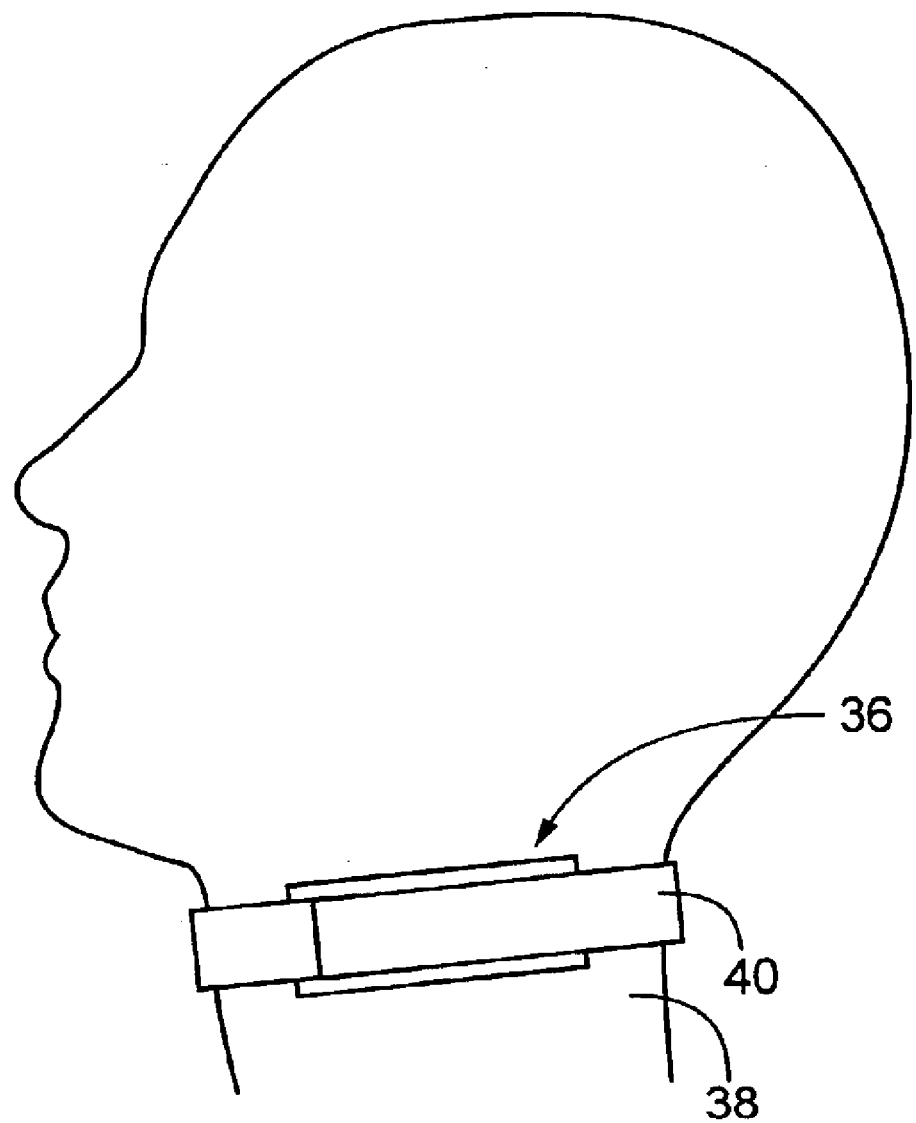
Figure 3:
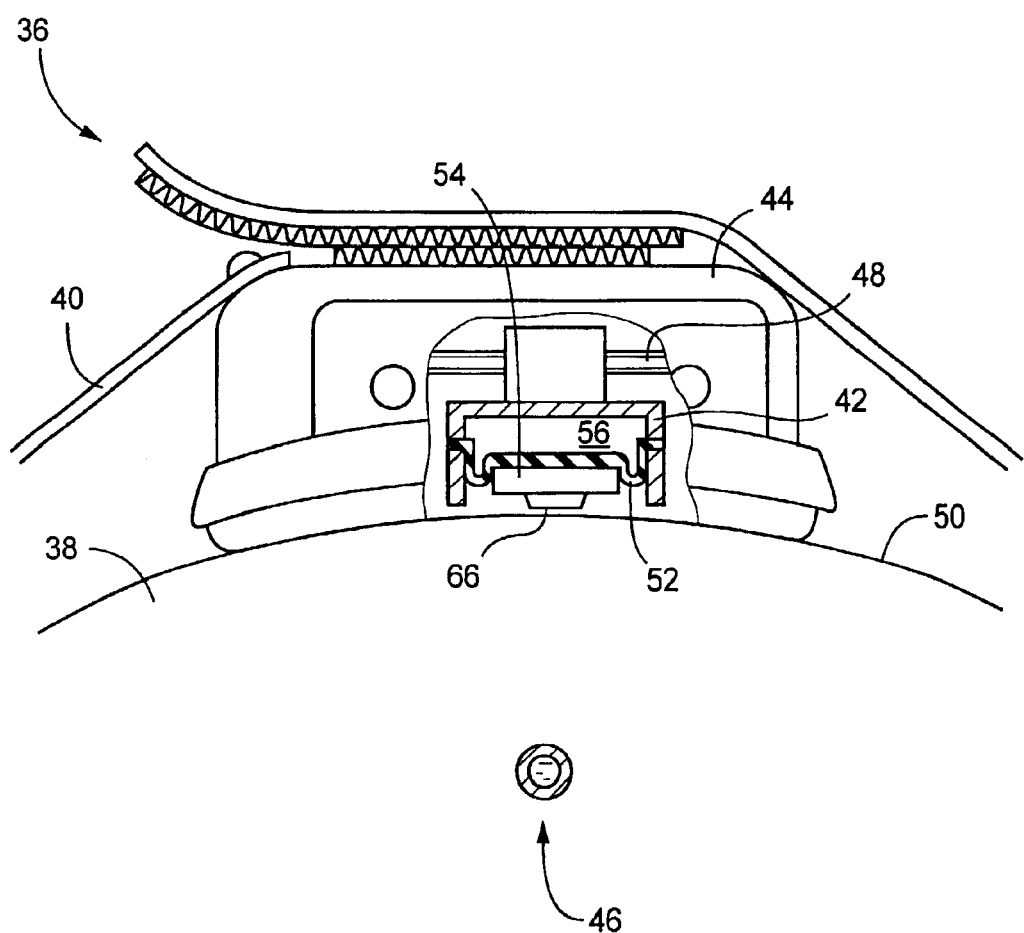

The present circulatory-organ evaluating apparatus 10 includes a pressure-pulse-wave detecting probe 36, shown in FIG. 2, that functions as a carotid-pulse-wave detecting device. The pressure-pulse-wave detecting probe 36 is worn on a cervical portion 38 of the patient, as shown in FIG. 2, with the help of a band 40. As shown in detail in FIG. 3, the pressure-pulse-wave detecting probe 36 includes a container-like sensor housing 42; a case 44 which accommodates the sensor housing 42; and a feed screw 48 which is threadedly engaged with the sensor housing 42 and is rotated by an electric motor, not shown, provided in the case 44 so as to move the sensor housing 42 in a widthwise direction of a carotid artery 46. With the help of the band, the pressure-pulse-wave detecting probe 36 is detachably attached to the cervical portion 38, such that an open end of the sensor housing 42 is opposed to a body surface 50 of the cervical portion 38.

In addition, the pressure-pulse-wave detecting probe 36 includes a pressure-pulse-wave sensor 54 which is secured via a diaphragm 52 to an inner wall of the sensor housing 42, such that the sensor 54 is movable relative to the housing 42 and is advanceable out of the open end of the same 42. The sensor housing 42, the diaphragm 52, etc. cooperate with one another to define a pressure chamber 56, which is supplied with a pressurized air from an air pump 58 via a pressure-control valve 60, as shown in FIG. 1, so that the pressure-pulse-wave sensor 54 is pressed against the body surface 50 with a pressing force corresponding to the air pressure in the pressure chamber 56.

The sensor housing 42 and the diaphragm 52 cooperate with each other to provide a pressing device 62 which presses the pressure-pulse-wave sensor 54 against the carotid artery 46, and the feed screw 48 and the not-shown motor cooperate with each other to provide a widthwise-direction moving device 64 which moves the pressure-pulse-wave sensor 54 in the widthwise direction of the carotid artery 46 and thereby changes a pressing position where the sensor 54 is pressed on the body surface 50.

Figure 4:
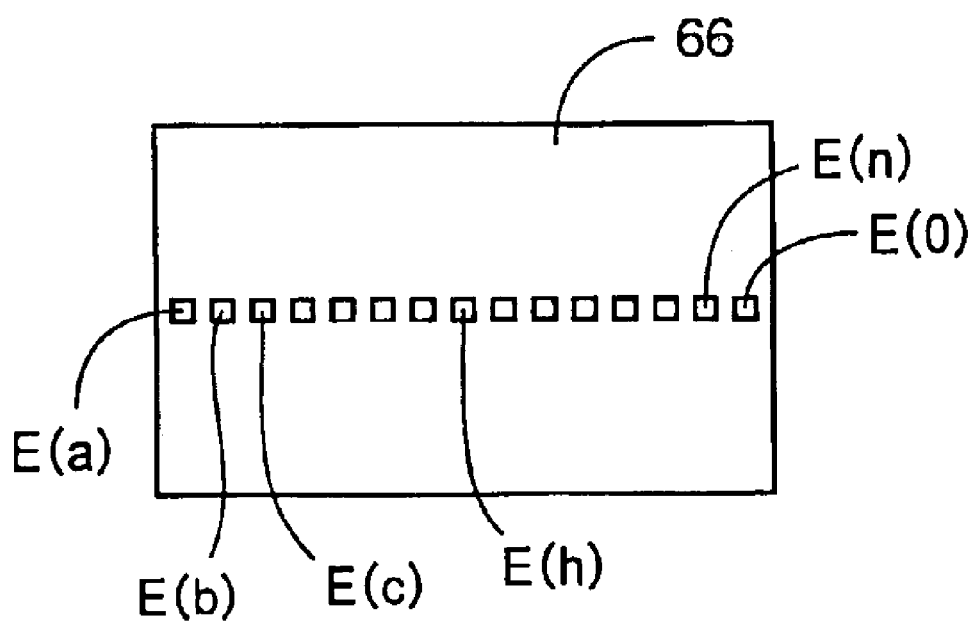

The pressure-pulse-wave sensor 54 has a pressing surface 66, and a number of semiconductor pressure sensing elements (hereinafter, referred to as the "pressure sensing elements") E which are arranged in the pressing surface 66 at a regular interval in the widthwise direction of the carotid artery 46, i.e., in the direction of movement of the sensor 54 parallel to the feed screw 48, over a length greater than the diameter of the carotid artery 46. For example, as shown in FIG. 4, fifteen pressure sensing elements E(a), E(b), . . . , E(o) are arranged at a regular interval of, e.g., 0.6 mm.

Figure 5:
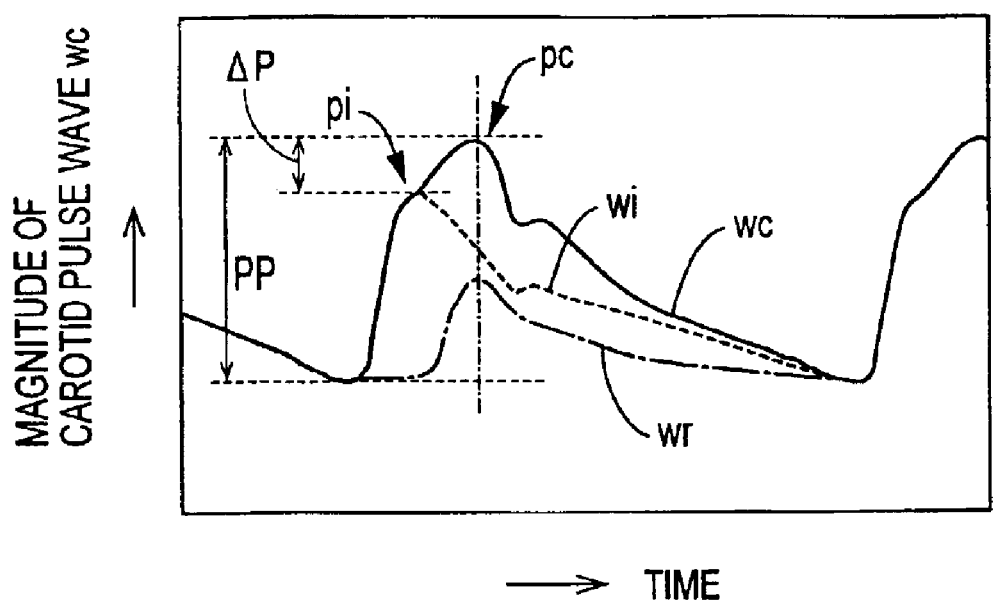

The pressure-pulse-wave detecting probe 36, constructed as described above, is pressed against the body surface 50 of the cervical portion 38 right above the carotid artery 46, so that the pressure-pulse-wave sensor 54 detects a pressure pulse wave (i.e., a carotid pulse wave, wc) which is produced from the carotid artery 46 and is transmitted to the body surface 50, and supplies a pressure-pulse-wave signal, SM2, representing the detected carotid pulse wave wc, to the control device 32 via an A/D converter, not shown. An example of the carotid pulse wave wc represented by the pressure-pulse-wave signal SM2 continuously supplied from the pressure-pulse-wave sensor 54 is indicated at solid line in FIG. 5.

Back to FIG. 1, the circulatory-organ evaluating apparatus 10 further includes a heart-sound microphone 68, an input device 70, and a memory device 72. The heart-sound microphone 68 is attached, with an adhesive tape, not shown, or the like, to a chest, not shown, of the patient. The microphone 68 incorporates a piezoelectric element, not shown, which converts heart sounds produced from the patient's heart, into an electric signal, i.e., a heart-sound signal, SH. A heart-sound-signal amplifier 74 includes four sorts of filters, not shown, which cooperate with one another to attenuate a low-pitch component having a great energy and thereby amplifies and filters a high-pitch component of the heart-sound signal SH supplied from the microphone 68. The heart-sound signal SH amplified and filtered by the amplifier 74 is supplied to the control device 32 via an A/D converter, not shown.

The input device 70 includes a keyboard, not shown, which is operated by an operator such as a doctor to input an identification code and a stature, T, of the patient. The input device 70 supplies respective signals representing the inputted subject's identification code and stature T, to the control device 32.

The memory device 72 is provided by a well-known memory such as a magnetic disk, a magnetic tape, or a non-volatile semiconductor memory, and stores, in a memory area allotted for each of a plurality of patients, a blood pressure, BP, an augmentation index, AI, and a pulse-wave velocity, PWV, of the each patient that are determined by the electronic control device 32.

The electronic control device 32 is provided by a so-called microcomputer including a CPU 76, a ROM (read only memory) 77, a RAM (random access memory) 78, and an I/O (input-and-output) port, not shown. The CPU 76 processes signals according to the control programs pre-stored in the ROM 77 by utilizing the temporary-storage function of the RAM 78, and supplies drive signals via the I/O port to the air pumps 24, 58 and the pressure control valves 18, 60 so as to control the cuff pressure PC and the pressure in the pressure chamber 56. Moreover, the CPU 76 determines, based on the cuff-pulse-wave signal SM1, the pressure-pulse-wave signal SM2, the cuff-pressure signal SC, and the heart-sound signal SH, each supplied to the control device 32, a blood pressure BP, an augmentation index AI, and a pulse-wave velocity PWV of each patient, and controls a display device 79 and the memory device 72.

Figure 6:
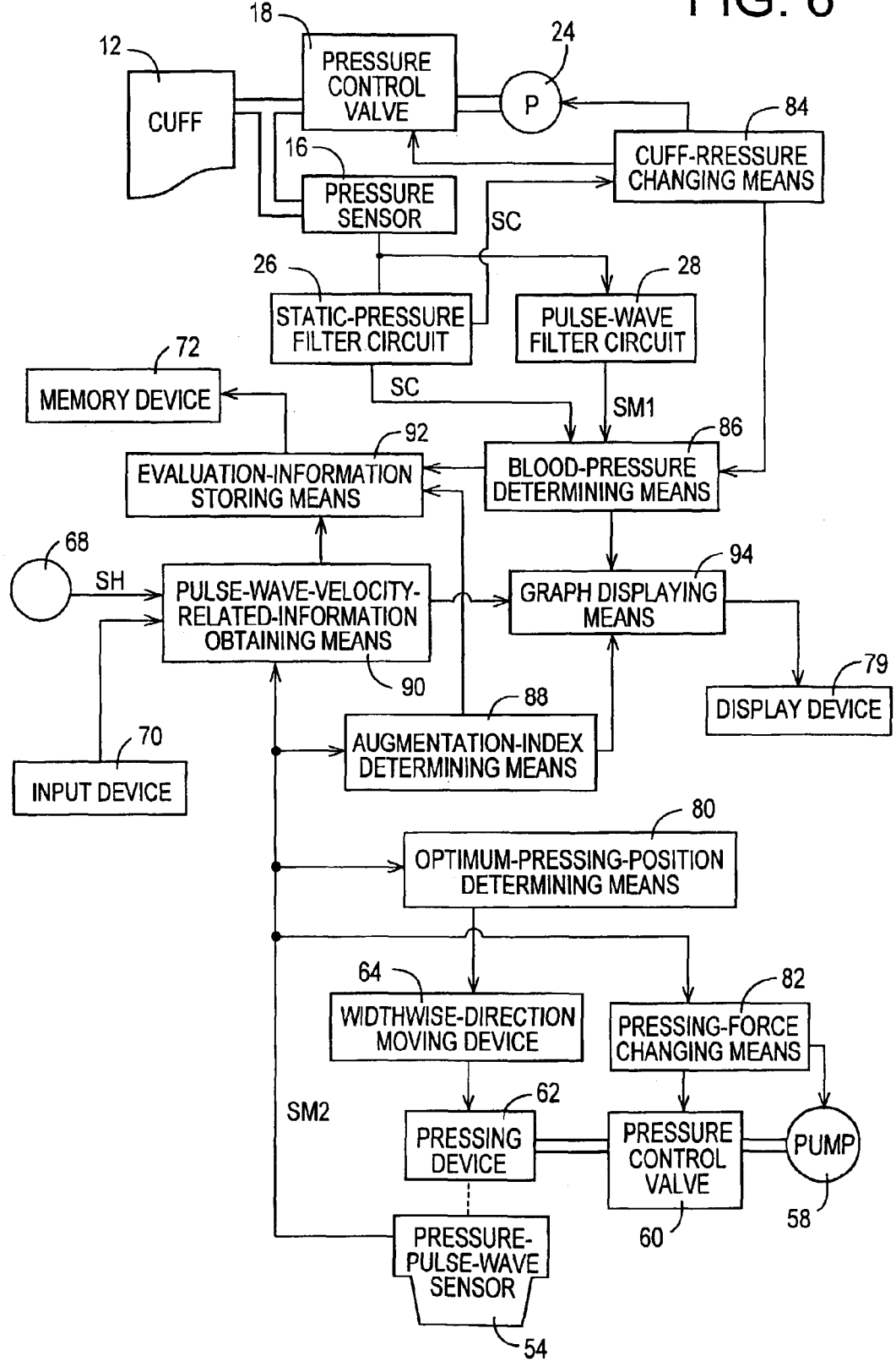
FIG. 6 is a diagrammatic view for explaining essential control functions of an electronic control device of the apparatus of FIG. 1.

FIG. 6 is a diagrammatic view for explaining essential control functions of the electronic control device 32 of the circulatory-organ evaluating apparatus.

An optimum-pressing-position determining device or means 80 judges whether a prescribed pressing-position changing condition is satisfied, i.e., whether one (hereinafter, referred to as the "highest-pressure sensing element, EM") of the pressure sensing elements E of the pressure-pulse-wave sensor 54 that detects the highest pressure of the respective pressures detected by all the elements E is positioned in one of prescribed opposite end portions of the array of pressure sensing elements E. Each of the prescribed opposite end portions of the array of elements E may be a range having a prescribed length including a corresponding one of the opposite ends of the array of elements E, or a range accommodating a prescribed number of elements E including a corresponding one of the respective elements E located at the opposite ends of the array. When this pressing-position changing condition is satisfied, the determining means 80 carries out the following pressing-position changing operation: After the pressing device 62 once moves the pressure-pulse-wave sensor 54 away from the body surface 50, the widthwise-direction moving device 64 moves the pressing device 62 and the sensor 54 over a prescribed distance, and then the pressing device 62 presses the sensor 54 with a prescribed, considerably small, first pressing force HDP1 that would be smaller than an optimum pressing force HDPO, described later. In this state, the determining means 80 judges again whether the prescribed pressing-position changing condition is satisfied. The determining means 80 repeats carrying out the above-described operation and judgment till the pressing-position changing condition is not satisfied any longer, preferably till the highest-pressure sensing element EM is positioned in a prescribed middle portion of the array of elements E. The length, or element number, employed for defining each of the opposite end portions of the array of elements E is prescribed based on the diameter of the artery (i.e., the carotid artery 46) to be pressed by the pressure-pulse-wave sensor 54, and may be one fourth of the diameter.

A pressing-force changing device or means 82 changes, after the optimum-pressing-position determining means 80 positions the pressure-pulse-wave sensor 54 at the optimum pressing position, a pressing force HDP (i.e., a hold-down pressure) applied by the pressing device 62 to the sensor 54, within a prescribed pressing-force range, either stepwise in response to each heartbeat of the patient or continuously at a prescribed, considerably low rate. Based on the carotid pulse wave wc obtained during the changing of the pressing force HDP, the changing means 82 determines an optimum pressing force HDPO and maintains the pressing force applied by the pressing device 62 to the sensor 54, at the thus determined optimum pressing force HDPO. Here, the optimum pressing force HDPO is so determined that a pulse pressure PP of the carotid pulse wave wc detected by the highest-pressure sensing element EM pressed with the pressing force HDP (i.e., a pressure difference obtained by subtracting a pressure corresponding to a minimum magnitude, from a pressure corresponding to a maximum magnitude, of one heartbeat-synchronous pulse of the carotid pulse wave wc) may not be smaller than a predetermined lower-limit pulse pressure PPL. The lower-limit pulse pressure PPL is experimentally determined, in advance, as a value which assures that a clear carotid pulse wave wc can be detected. If a pulse pressure PP is too small, a clear carotid pulse wave wc cannot be obtained.

A cuff-pressure changing device or means 84 operates, based on the cuff-pressure signal SC supplied from the static-pressure filter circuit 26, the pressure control valve 18 and the air pump 24 so as to quickly increase the cuff pressure PC to a prescribed target pressure $PC_M$ (e.g., 180 mmHg) that would be higher than a systolic blood pressure $BP_{SYS}$ of the patient and, subsequently, slowly decrease the cuff pressure at a rate of, e.g., 2 or 3 mmHg/sec. After a blood-pressure determining device or means 86, described below, determines blood-pressure values BP of the patient, the changing means 84 releases the cuff pressure to an atmospheric pressure.

The blood-pressure determining means 86 determines, based on the cuff-pressure signal SC continuously supplied from the static-pressure filter circuit 26, and the cuff-pulse-wave signal SM1 continuously supplied from the pulse-wave filter circuit 28, each during the slow decreasing of the cuff pressure PC under the control of the cuff-pressure changing means 84, a systolic blood pressure $BP_{SYS}$, a mean blood pressure $BP_{MEAN}$, and a diastolic blood pressure $BP_{DIA}$ of the patient, according to well-known oscillometric method.

An augmentation-index determining device or means 88 first determines respective times of occurrence of respective peak points, pi and pr, of an incident-wave component, wi, and a reflected-wave component, wr, which are contained in a heartbeat-synchronous pulse of the carotid pulse wave wc continuously detected by the highest-pressure sensing element EM of the pressure-pulse-wave sensor 54 in the state in which the pressing force HDP applied to the sensor 54 is maintained at the optimum pressing force HDPO. Then, the determining means 88 determines a pressure difference, ΔP, by subtracting a pressure corresponding to a magnitude of the carotid pulse wave wc at the time of occurrence of the peak point pi of the incident-wave component from a pressure corresponding to a magnitude of the carotid pulse wave wc at the time of occurrence of the peak point pr of the reflected-wave component wr. In addition, the determining means 88 determines a pulse pressure PP of the heartbeat-synchronous pulse of the carotid pulse wave wc. And, the determining means 88 calculates an augmentation index AI by substituting the following Expression 1 with the thus determined pressure difference ΔP and pulse pressure PP:

$$AI=(\Delta P/PP)\times 100 (\%) \qquad \text{(Expression 1)}$$

Here, the manner in which the time of occurrence of peak point pi of incident-wave component wi of the carotid pulse wave wc is explained. The carotid pulse wave wc contains the incident-wave component wi, indicated at broken line in FIG. 5, and the peak point pi of the incident-wave component wi corresponds to an inflection point or a local-maximum point of the composite carotid pulse wave wc (i.e., observed wave) that occurs between a rising point (i.e., a minimum point) and a peak point, pc, of the composite wave wc. In the example shown in FIG. 5, the peak point pi of the incident-wave component wi corresponds to an inflection point of the observed wave wc. To this end, the determining means 88 subjects the continuously obtained pressure-pulse-wave signal SM2 to a mathematical treatment commonly used to identify an inflection or local-maximum point; such as a differentiation treatment or a filter treatment.

The time of occurrence of peak point pr of the reflected-wave component wr is generally defined as a time of occurrence of the first local-maximum point following the peak point pi of the incident-wave component wi. Therefore, in the case, shown in FIG. 5, where a peak point pi of an incident-wave component wi does not coincide with a peak point pc of a carotid pulse wave wc, the time of occurrence of peak point pc of the carotid pulse wave wc is determined as the time of occurrence of peak point pr of reflected-wave component wr. On the other hand, in the case where a peak point pi of an incident-wave component wi is so large that the peak point pi of incident-wave component wi also defines a peak point pc of a carotid pulse wave wc, the time of occurrence of the first local-maximum point following the peak point pi of incident-wave component wi is determined as the time of occurrence of peak point pr of reflected-wave component wr.

A pulse-wave-velocity-related-information obtaining device or means 90 first determines a prescribed point (e.g., a starting point of second heart sound, II) of a heart-sound waveform represented by the heart-sound signal SH continuously supplied from the heart-sound microphone 68, and a prescribed point (e.g., a dicrotic notch) of the carotid pulse wave wc, represented by the pressure-pulse-wave signal SM2, that corresponds to the prescribed point of the heart-sound waveform, and then determines a time difference between a time of detection of the prescribed point of the heart-sound waveform and a time of detection of the prescribed point of the carotid pulse wave wc. This time difference is a pulse-wave propagation time, DT, that is needed for the carotid pulse wave wc to propagate from the patient's aortic valve to the cervical portion 38 where the pressure-pulse-wave detecting probe 36 is worn. In addition, the obtaining means 90 determines, according to a predetermined relationship between stature T and propagation distance L, represented by the following Expression 2, and based on the patient's stature T supplied from the input device 70, a propagation distance L between the patient's aortic valve and the cervical portion 38 where the probe 36 is worn, and finally determines a pulse-wave velocity PWV (cm/sec) according to the following Expression 3 and based on the thus obtained propagation distance L and pulse-wave propagation time DT:

$$L=aT+b \qquad \text{(Expression 2)}$$

(a and b are experimentally determined constants)

$$PWV=L/DT \qquad \text{(Expression 3)}$$

An evaluation-information storing device or means 92 stores, in a certain memory area of the memory device 72, a set of circulatory-organ evaluation information including the blood-pressure values BP determined by the blood-pressure determining means 86, the augmentation index AI determined by the augmentation-index determining means 88, and the pulse-wave velocity PWV obtained by the pulse-wave-velocity-related-information obtaining means 90, such that the set of evaluation information is associated with the identification code identifying each patient and a date (or a date and a time) when the set of evaluation information is obtained.

A graph displaying device or means 94 operates the display device 79 to display a three-dimensional graph having a blood-pressure axis, an augmentation-index axis, and a pulse-wave-velocity-related-information axis. In addition, the graph displaying means 96 operates the display device 79 to display, in the three-dimensional graph, a symbol representing the blood-pressure values BP determined by the blood-pressure determining means 86, the augmentation index AI determined by the augmentation-index determining means 88, and the pulse-wave velocity PWV obtained by the pulse-wave-velocity-related-information obtaining means 90. If the memory device 72 stores one or more past sets of evaluation information that had been obtained from the patient, the graph displaying means 94 operates the display device 79 to additionally display, in the three-dimensional graph, one or more symbols representing the one or more past sets of evaluation information.

Figure 7:
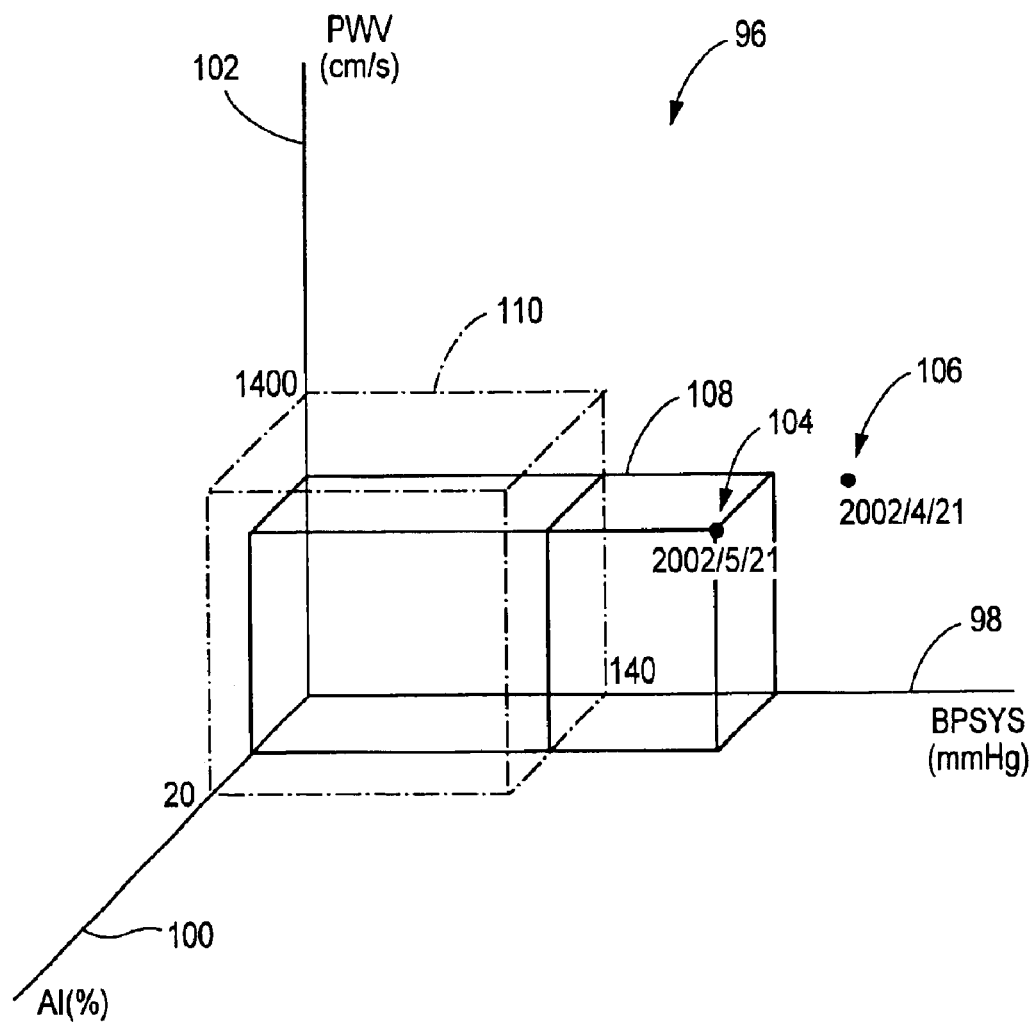
FIG. 7 is a view showing a three-dimensional scatter diagram as an example of a three-dimensional graph which is displayed on a display device by a graph displaying means shown in FIG. 6.

FIG. 7 shows an example of the three-dimensional graph displayed by the display device 79 under control of the graph displaying means 94, that is, a three-dimensional scatter diagram 96 as a sort of three-dimensional graph. The three-dimensional scatter diagram 96 has a systolic-blood-pressure axis 98, an augmentation-index axis 100, and a pulse-wave-velocity axis 102, and shows a circle and a day 104 representing a systolic blood pressure value $BP_{SYS}$, an augmentation index AI, and a pulse-wave velocity PWV that are measured in the current measuring operation carried out on the day, and a circle and a day 106 representing a systolic blood pressure value $BP_{SYS}$, an augmentation index AI, and a pulse-wave velocity PWV that were measured in the past measuring operation carried out on the day and are stored in the memory device 72. Thus, a person such as a doctor can recognize respective time-wise changes of the systolic blood pressure value $BP_{SYS}$, augmentation index AI, and pulse-wave velocity PWV of the patient. In addition, the diagram 96 shows a measurement figure 108 representing the three values measured in the current measurement, and having a rectangular parallelepiped shape.

The three-dimensional scatter diagram 96 additionally shows a standard figure 110 representing respective upper-limit values of respective normal ranges (i.e., respective standard values) of the systolic blood pressure value $BP_{SYS}$, augmentation index AI, and pulse-wave velocity PWV, and having a cubic shape. In the example shown in FIG. 7, the respective upper-limit values of respective normal ranges of the systolic blood pressure value $BP_{SYS}$, augmentation index AI, and pulse-wave velocity PWV are 140 mmHg, 20%, and 1,400 cm/s, respectively.

By comparing the measurement figure 108, or the position of the circle 104, with the standard figure 110 in the three-dimensional scatter graph 96 shown in FIG. 7, a person can easily recognize that the patient's augmentation index AI and pulse-wave velocity PWV are normal but the patient's systolic blood pressure $BP_{SYS}$ is too high. In addition, by comparing the circle 104 with the circle 106, the person can recognize that the patient's systolic blood pressure $BP_{SYS}$ is being improved.

Figure 8:
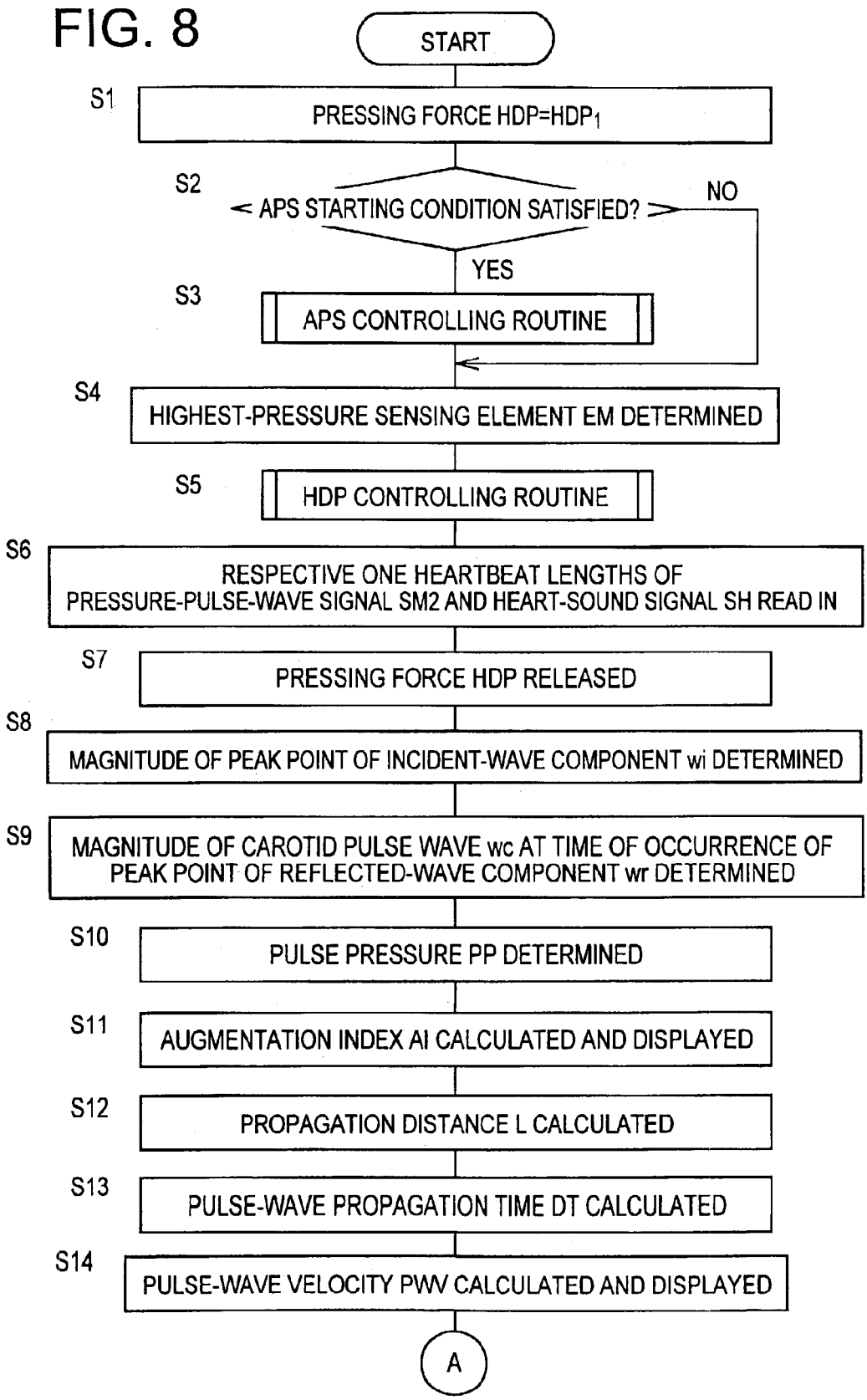
FIG. 8 is a flow chart for explaining a portion of the control functions of a CPU (central processing unit) of the control device, shown in the diagrammatic view of FIG. 6.
Figure 9:
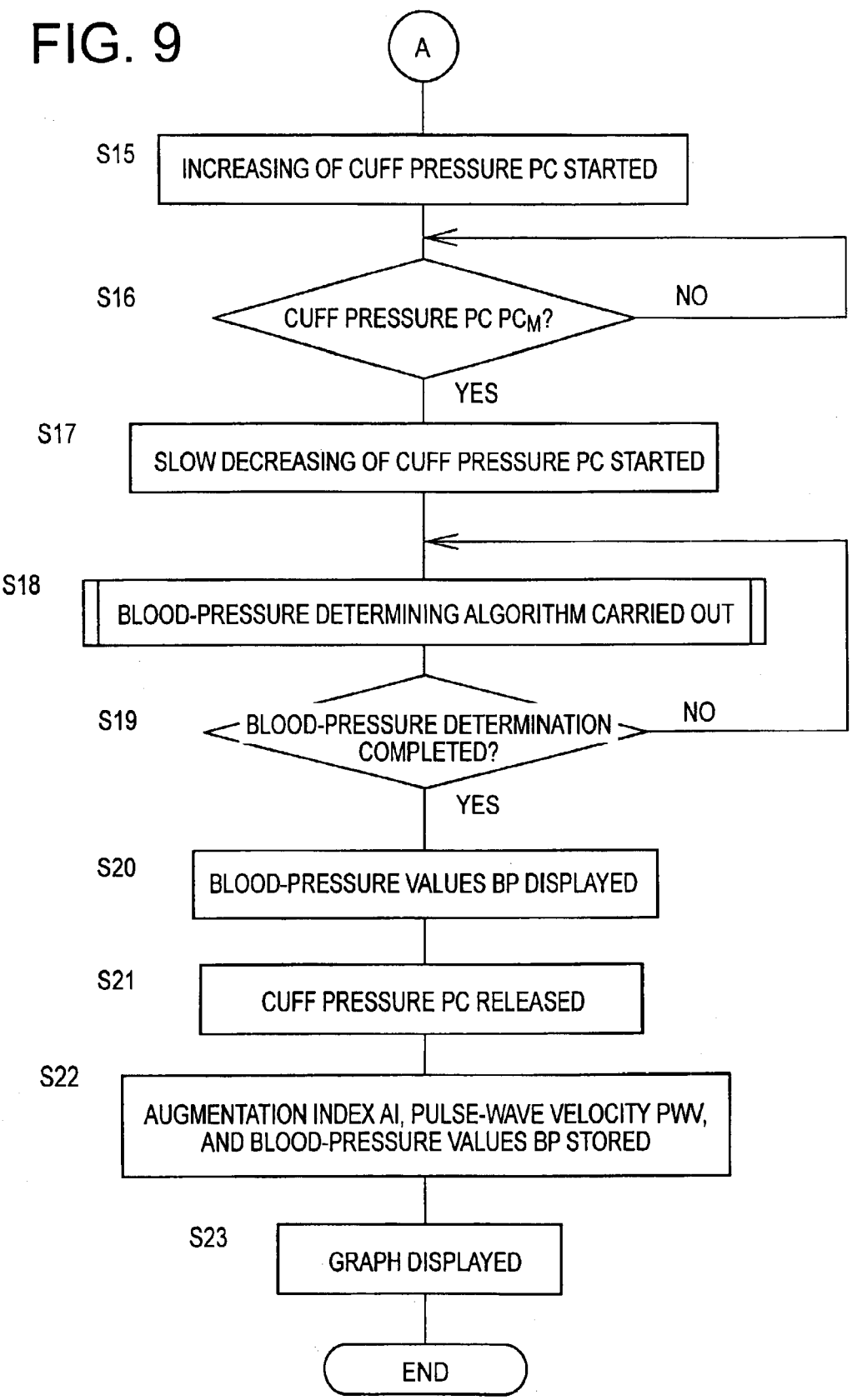
FIG. 9 is a flow chart for explaining another portion of the control functions of the CPU, shown in the diagrammatic view of FIG. 6.

FIGS. 8 and 9 are flow charts for explaining the control functions of the CPU 76, shown in the diagrammatic view of FIG. 6.

In FIG. 8, first, the CPU carries out Steps S1 through S3 (hereinafter, the term "Step(s)" is omitted) corresponding to the optimum-pressing-position determining means 80. First, at S1, the CPU operates the pressing device 62 to change the pressure in the pressure chamber 56, thereby changing the pressing force HDP applied to the pressure-pulse-wave sensor 54, to the prescribed first pressing force HDP1. The first pressing force HDP1 is experimentally determined, in advance, such that an S/N ratio of the carotid pulse wave wc detected by each of the pressure sensing elements E is so great as to be able to determine, with sufficiently high accuracy, a magnitude of a peak point pc of a heartbeat-synchronous pulse of the carotid pulse wave wc.

Subsequently, at S2, the CPU judges whether the pressing-position changing condition (i.e., the APS starting condition) is satisfied, i.e., whether a current highest-pressure sensing element EM as one of the pressure sensing elements E of the pressure-pulse-wave sensor 54 is positioned in one of the prescribed opposite end portions of the array of elements E. If a negative judgment is made at S2, the control jumps to S4, described later.

On the other hand, if a positive judgment is made at S2, that is, if the current position of the pressure-pulse-wave sensor 54 relative to the carotid artery 46 is not appropriate, the control goes to S3, i.e., an APS controlling routine in which the pressure-pulse-wave sensor 54 is positioned at an optimum pressing position where the current highest-pressure sensing element EM is located at substantially the middle of the array of elements E. More specifically described, the CPU carries out the following pressing-position changing operation: After the pressing device 62 once moves the pressure-pulse-wave sensor 54 away from the body surface 50, the widthwise-direction moving device 64 moves the pressing device 62 and the sensor 54 over a prescribed distance, and then the pressing device 62 presses again the sensor 54 with the first pressing force HDP1. In this state, the CPU judges again whether the prescribed pressing-position changing condition is satisfied. The CPU repeats those actions and judgment till the pressing-position changing condition is not satisfied any longer, more specifically described, till the current highest-pressure sensing element EM is positioned in the prescribed middle portion of the array of elements E.

After the pressure-pulse-wave sensor 54 is positioned at the optimum pressing position at S3, or if a negative judgment is made at S2, the control goes to S4 to determine the current highest-pressure sensing element EM as a final highest-pressure sensing element EM of the sensor 54. S4 is followed by S5 corresponding to the pressing-force determining means 82, i.e., an HDP controlling routine. More specifically described, the CPU operates the pressing device 62 so that the pressing force HDP applied to the pressure-pulse-wave sensor 54 is continuously increased from the first pressing force HDP1. During this increasing of the pressing force HDP, the CPU determines an optimum pressing force HDPO at which a pulse pressure PP of a heartbeat-synchronous pulse of the carotid pulse wave wc detected by the highest-pressure sensing element EM determined at S4 exceeds the prescribed lower-limit pulse pressure PPL, and maintains the pressing force HDP applied to the sensor 54, at the thus determined optimum pressing force HDPO.

Then, the control goes to S6 where the CPU reads in respective one-heartbeat lengths of the pressure-pulse-wave signal SM2 supplied from the highest-pressure sensing element EM determined at S4 and the heart-sound signal SH supplied from the heart-sound microphone 68. Then, the control goes to S7 to stop the air pump 58 and operate the pressure control valve 60 so that the pressing force HDP applied to the sensor 54 is decreased down to an atmospheric pressure.

Subsequently, the control proceeds with S8 through S11 corresponding to the augmentation-index calculating means 88. First, at S8, the CPU subjects, to a fourth-order differentiation, a heartbeat-synchronous pulse of the carotid pulse wave wc that is represented by the one-heartbeat length of the pressure-pulse-wave signal SM2 read in at S6, more specifically described, a portion of the carotid pulse wave wc that is located between a rising point and a peak point pc of the pulse, so as to identify an inflection point or a local-maximum point located between the rising point and the peak point pc. The CPU determines a magnitude of the thus identified inflection point or local-maximum point as a magnitude of the peak point pi of the incident-wave component wi.

Subsequently, at S9, the CPU determines a magnitude of the carotid pulse wave wc at the time of occurrence of the peak point of reflected-wave component wr. More specifically described, in the case where the peak point pi of incident-wave component wi, determined at S8, does not coincide with a maximum point of the heartbeat-synchronous pulse of the carotid pulse wave wc, a magnitude of the maximum point of the heartbeat-synchronous pulse of the carotid pulse wave wc is determined as the magnitude of the carotid pulse wave wc at the time of occurrence of the peak point of the reflected-wave component wr. On the other hand, in the case where the peak point pi of the incident-wave component wi, determined at S8, coincides with the maximum point of the heartbeat-synchronous pulse of the carotid pulse wave wc, a magnitude of the first local-maximum point following the peak point pi of the incident-wave component wi is determined as the magnitude of the carotid pulse wave wc at the time of occurrence of the peak point of reflected-wave component wr.

Then, at S10, the CPU determines a pulse pressure PP of the heartbeat-synchronous pulse of the carotid pulse wave wc, read in at S6. S10 is followed by S11 to calculate a pressure difference $\Delta P$ by subtracting the magnitude of the carotid pulse wave wc at the time of occurrence of the peak point of the incident-wave component wi, determined at S8, from the magnitude of the carotid pulse wave wc at the time of occurrence of the peak point of the reflected-wave component wr, determined at S9. Additionally, the CPU calculates an augmentation index AI by substituting the augmentation-index calculating expression shown in the form of Expression 1, with the thus calculated pressure difference $\Delta P$ and the pressure difference PP determined at S10, and operates the display device 79 to display the thus calculated augmentation index AI in digits.

Then, the control goes to S12 through S14 corresponding to the pulse-wave-velocity-related-information obtaining means 90. At S12, the CPU calculates a propagation distance L by substituting Expression 2 with the stature T that had been inputted through the input device 72 before the current operation of the CPU is started. Subsequently, at S13, the CPU identifies a starting point of a second heart sound II based on the one-heartbeat length of the heart-sound signal SH, read in at S6, and a dicrotic-notch point of a heartbeat-synchronous pulse of the carotid pulse wave wc based on the one-heartbeat length of the pressure-pulse-wave signal SM2, read in at S6, and calculates, as a pulse-wave propagation time DT, a time difference between a time of detection of the starting point of the second heart sound II and a time of detection of the dicrotic-notch point of the carotid pulse wave wc. Then, at S14, the CPU calculates a pulse-wave velocity PWV by substituting Expression 3 with the propagation distance L and the propagation time DT respectively calculated at S12 and S13, and operates the display device 79 to display the thus calculated pulse-wave velocity PWV in digits.

Next, S15 and the following steps shown in FIG. 9 will be described. At S15, the CPU starts the air pump 24 and operate the pressure control valve 18 so as to start quickly increasing the cuff pressure PC. Subsequently, at S16, the CPU judges whether the cuff pressure PC has exceeded a target pressure $PC_M$ pre-set at 180 mmHg. S16 is repeated until a positive judgment is made, while the cuff pressure PC is quickly increased. Meanwhile, if a positive judgment is made at S16, the control goes to S17 to stop the air pump 24 and operate the pressure control valve 18 so as to start slowly decreasing the cuff pressure PC at a rate of about 3 mmHg/sec.

Next, the control goes to S18 to S20 corresponding to the blood-pressure determining means 86. At S18, the CPU determines, based on change of respective amplitudes of successive heartbeat-synchronous pulses of the brachial pulse wave wb represented by the cuff-pulse-wave signal SM1 continuously obtained during the slow decreasing of the cuff pressure PC, a systolic blood pressure $BP_{SYS}$, a mean blood pressure $BP_{MEAN}$, and a diastolic blood pressure $BP_{DIA}$ of the patient, according to well-known oscillometric blood-pressure determining algorithm. Then, at S19, the CPU judges whether the determination of the blood-pressure values BP has completed at S18.

S18 and S19 are repeated till a positive judgment is made at S19. Thus, the blood-pressure determining algorithm is continued. Meanwhile, if a positive judgment is made at S19, the control goes to S20 to operate the display device 79 to display the thus determined systolic, mean, and diastolic blood-pressure values $BP_{SYS}$, $BP_{MEAN}$, $BP_{DIA}$ in digits. Then, the control goes to S21 to operate the pressure control valve 18 to decrease the cuff pressure PC to an atmospheric pressure. In the present flow chart, S15 through S17 and S21 correspond to the cuff-pressure changing means 84.

Then, the control goes to S22 corresponding to the evaluation-information storing means 92. At S22, the CPU stores, in a certain memory area of the memory device 72, the augmentation index AI calculated at S11, the pulse-wave velocity PWV calculated at S14, and the systolic blood pressure $BP_{SYS}$ calculated at S18, as a set of evaluation information obtained, from the patient identified by the identification code inputted before the current operation of the CPU is started, together with data indicative of a date when the set of evaluation information is obtained from the patient.

Then, the control goes to S23 corresponding to the graph displaying means 94. At S23, the CPU operates the display device 79 to display the three-dimensional scatter diagram 96, as shown in FIG. 7, and additionally display, in the graph 96, the circle 104 and the measurement figure 108 each of which represents the augmentation index AI calculated at S11, the pulse-wave velocity PWV calculated at S14, and the systolic blood pressure $BP_{SYS}$ calculated at S18; the standard figure 110; and the circle 106 representing the past set of evaluation information that has been stored, in the memory device 72, for the patient identified by the identification code inputted before the current operation of the CPU is started.

In the above-described embodiment, a person such as a doctor can graphically recognize, from the three-dimensional scatter diagram 96 displayed on the display device 79, the respective measured values of the systolic blood pressure $BP_{SYS}$, the augmentation index AI, and the pulse-wave velocity PWV of the patient. Thus, the person can easily make a total evaluation of the circulatory organ of the patient based on the three parameters.

Moreover, in the above-described embodiment, the three-dimensional scatter diagram 96 shows the standard figure 110 representing the respective upper limits of the respective normal ranges of systolic blood pressure $BP_{SYS}$, augmentation index AI, and pulse-wave velocity PWV. Therefore, the person can more easily evaluate the circulatory organ by comparing the measurement figure 108 or the circle 104 representing the respective measured values of the systolic blood pressure $BP_{SYS}$, the augmentation index AI, and the pulse-wave velocity PWV of the patient, with the standard figure 110.

Moreover, in the above-described embodiment, the three-dimensional scatter diagram 96 shows the circles 104, 106 that cooperate with each other to represent the respective timewise changes of the systolic blood pressure $BP_{SYS}$, the augmentation index AI, and the pulse-wave velocity PWV of the patient. Thus, the person can graphically recognize the respective timewise changes of the systolic blood pressure $BP_{SYS}$, the augmentation index AI, and the pulse-wave velocity PWV of the patient, and accordingly can easily recognize the timewise change of dynamic function of the circulatory organ of the patient. Therefore, the person can easily evaluate the effect of medication or the improvement of patient's habits.

While the present invention has been described in its preferred embodiment by reference to the drawings, it is to be understood that the invention may otherwise be embodied.

Figure 10:
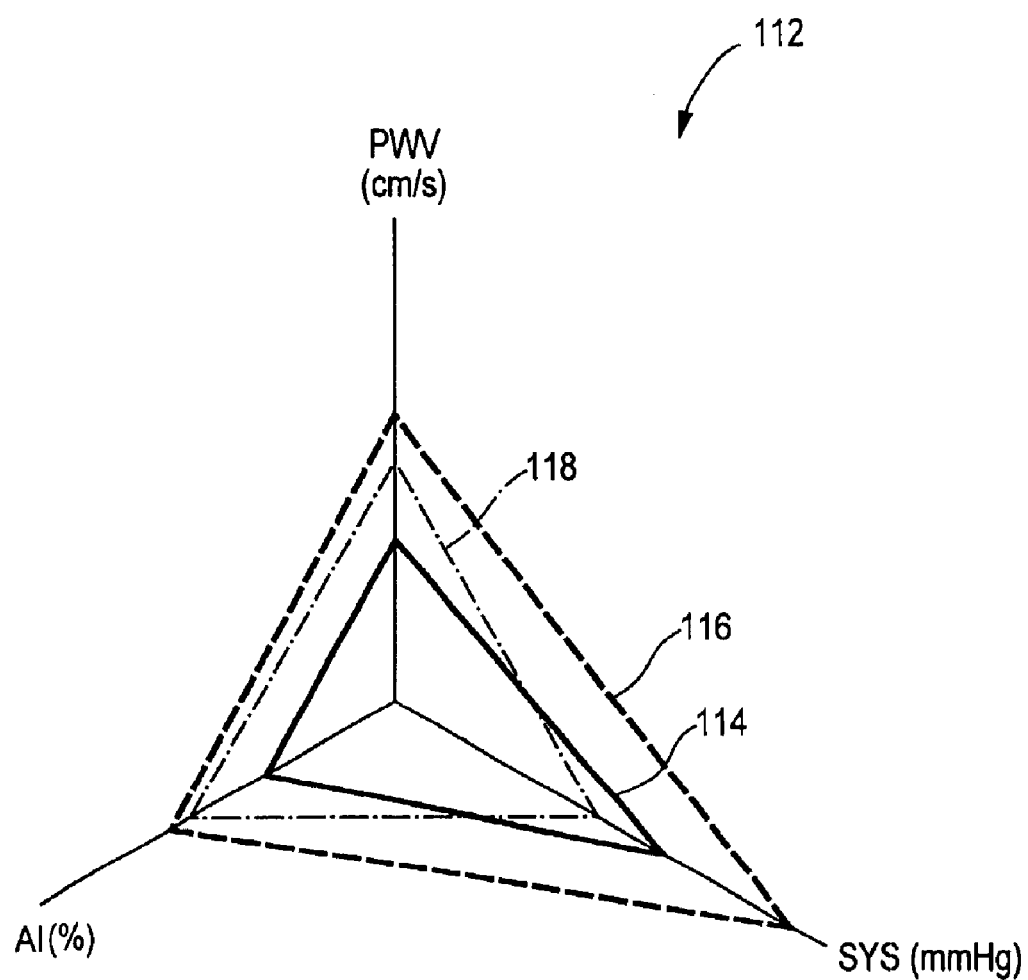
FIG. 10 is a view showing a radar chart as another example of the three-dimensional graph which is displayed on the display device by the graph displaying means shown in FIG. 6.

For example, in the illustrated embodiment, the three-dimensional scatter diagram 96 is used as a sort of three-dimensional graph. However, other sorts of three-dimensional graphs may be used; such as a radar chart 112 as shown in FIG. 10. In FIG. 10, a solid-line triangle 114 represents respective values of systolic blood pressure $BP_{SYS}$, augmentation index AI, and pulse-wave velocity PWV of a patient, measured in a current measuring operation; a broken-line triangle 116 represents respective values of systolic blood pressure $BP_{SYS}$, augmentation index AI, and pulse-wave velocity PWV of the same patient, measured in the preceding or last measuring operation; and a one-dot-chain-line triangle 118 represents respective upper-limit values (i.e., respective standard values) of systolic blood pressure $BP_{SYS}$, augmentation index AI, and pulse-wave velocity PWV.

Also, in the illustrated embodiment, the three-dimensional scatter diagram 96 represents the systolic blood pressure $BP_{SYS}$, the augmentation index AI, and the pulse-wave velocity PWV of the subject. However, the systolic blood pressure $BP_{SYS}$, may be replaced with the mean or diastolic blood pressure $BP_{MEAN}$, $BP_{DIA}$, and the pulse-wave velocity PWV may be replaced with the pulse-wave propagation time DT.

Also, in the illustrated embodiment, the display device 79 displays the three-dimensional scatter diagram 96 as the three-dimensional graph. However, it is possible to obtain another or other sorts of circulatory-organ evaluation information (e.g., heart rate, HR) and display a four- or higher-dimensional graph additionally representing the other sorts of evaluation information.

Also, the illustrated circulatory-organ evaluating apparatus 10 has the functions of measuring the blood pressure BP, the augmentation index AI, and the pulse-wave velocity PWV of living subject. However, the illustrated apparatus 10 may be so modified as not to have those functions. In the latter case, other devices may measure those parameters, and supply the respective measured values of the parameters to the thus modified apparatus 10.

Also, the illustrated apparatus 10 substantially simultaneously measure the blood pressure BP, the augmentation index AI, and the pulse-wave velocity PWV of living subject. However, it is not essentially required to substantially simultaneously measure those parameters, so long as the respective measured values of those parameters are simultaneously displayed.

Also, in the illustrated embodiment, the blood pressure BP is measured at the brachial portion 14, the augmentation index AI is measured at the cervical portion 38, and the pulse-wave velocity PWV is measured at the portion between the subject's heart (i.e., aortic valve) and the cervical portion 38. However, those parameters may be measured at other portions of the subject. For example, blood pressure BP may be measured at a femoral portion or an ankle; augmentation index AI may be measured at a brachial portion 14; and pulse-wave velocity PWV may be measured at a portion between a brachium and an ankle.

Also, the generally-used augmentation-index calculating expression (i.e., Expression 1) employs the pulse pressure PP as its denominator. However, though the denominator may be replaced with the magnitude of the carotid pulse wave wc at the time of occurrence of peak point of the incident-wave component wi, a value calculated according to the thus modified expression adequately reflects a degree of arteriosclerosis of the subject. Therefore, the pulse pressure PP in Expression 1 may be replaced with the magnitude of the carotid pulse wave wc at the time of occurrence of peak point of the incident-wave component wi.

The present invention may be embodied with other various changes without departing from the spirit of the invention.

What is claimed is:

1. A circulatory-organ evaluating apparatus for evaluating a circulatory organ of a living subject, comprising:
   a display device which displays a three-dimensional graph representing a blood pressure, an augmentation index, and a pulse-wave-velocity-related information of the subject; and
   a control device which controls the display device to simultaneously and graphically display the blood pressure, the augmentation index, and the pulse-wave-velocity-related information of the subject.

2. A circulatory-organ evaluating apparatus recited in claim 1, wherein the three-dimensional graph includes a standard figure representing a standard blood pressure, a standard augmentation index, and standard pulse-wave-velocity-related information.

3. A circulatory-organ evaluating apparatus recited in claim 1, wherein the three-dimensional graph represents respective time-wise changes of the blood pressure, the augmentation index, and the pulse-wave-velocity-related information of the subject.

4. A circulatory-organ evaluating apparatus according to claim 3, further comprising a memory device which stores at least one past set of evaluation information including at least a blood pressure, an augmentation index, and pulse-wave-velocity-related information that were measured from the subject in at least one past measuring operation, wherein the control device controls, based on the set of evaluation information stored in the memory device, the display device to display the three-dimensional graph representing the respective time-wise changes of the blood pressure, the augmentation index, and the pulse-wave-velocity-related-information information of the subject.

5. A circulatory-organ evaluating apparatus according to claim 1, further comprising an input device which is operable by an operator to input identification information identifying the subject.

6. A circulatory-organ evaluating apparatus according to claim 1, further comprising:
   a blood-pressure measuring device which measures the blood pressure of the subject;
   an augmentation-index determining device which determines the augmentation index of the subject; and a pulse-wave-velocity-related-information obtaining device which obtains the pulse-wave-velocity-related information of the subject.

* * * * *